(12) United States Patent
Fujita (10) Patent No.: US 10,121,644 B2
(45) Date of Patent: Nov. 6, 2018

(54) MASS SPECTROMETER AND MASS SPECTROMETRY METHOD

(71) Applicant: SHIMADZU CORPORATION, Kyoto-shi, Kyoto (JP)

(72) Inventor: Shinjiro Fujita, Kameoka (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 15/110,306

(22) PCT Filed: Feb. 10, 2014

(86) PCT No.: PCT/JP2014/053015
§ 371 (c)(1),
(2) Date: Jul. 7, 2016

(87) PCT Pub. No.: WO2015/118681
PCT Pub. Date: Aug. 13, 2015

(65) Prior Publication Data
US 2016/0329203 A1  Nov. 10, 2016

(51) Int. Cl.
*H01J 49/00* (2006.01)
*H01J 49/16* (2006.01)
(Continued)

(52) U.S. Cl.
CPC ........ *H01J 49/165* (2013.01); *G01N 30/8631* (2013.01); *G01N 30/8651* (2013.01);
(Continued)

(58) Field of Classification Search
CPC .. H01J 49/165; H01J 49/0031; H01J 49/4215; H01J 49/24; H01J 49/168;
(Continued)

(56) References Cited

U.S. PATENT DOCUMENTS

2002/0125423 A1   9/2002  Ebeling et al.
2015/0219607 A1*  8/2015  Fujita ................... H01J 49/025
                                                       250/288

FOREIGN PATENT DOCUMENTS

JP   2005-539358 A   12/2005
JP   2008-053020 A    3/2008
(Continued)

OTHER PUBLICATIONS

Communication dated Jan. 23, 2017, from the European Patent Office in counterpart European Application No. 14881512.9.
(Continued)

*Primary Examiner* — Michael Maskell
(74) *Attorney, Agent, or Firm* — Sughrue Mion, PLLC (57) ABSTRACT

A mass spectrometer including an ionization source including an ESI probe (201), an ESI power source (24), a corona needle (202) and an APCI power source (24); an ionization condition storage section (41) for storing a plurality of ionization conditions related to the liquid sample, set by an analysis operator, with the ionization conditions differing from each other in the value of the ESI voltage or/and the value of the APCI voltage; a mass spectrometry executer (43) for conducting a mass spectrometry for an ion generated from the liquid sample using each of the plurality of ionization conditions; and a mass spectrometry result selector (44) for selecting, for each of the one or plurality of components, a mass spectrometry result in which the ion is detected with a suitable level of intensity for an analysis, from the mass spectrometry results respectively obtained for the plurality of ionization conditions.

13 Claims, 6 Drawing Sheets

(51) Int. Cl.
*H01J 49/10* (2006.01)
*G01N 30/86* (2006.01)
*H01J 49/24* (2006.01)
*H01J 49/42* (2006.01)
*G01N 30/72* (2006.01)

(52) U.S. Cl.
CPC ........ *H01J 49/0031* (2013.01); *H01J 49/107* (2013.01); *H01J 49/168* (2013.01); *H01J 49/24* (2013.01); *H01J 49/4215* (2013.01); *G01N 30/7266* (2013.01)

(58) Field of Classification Search
CPC .............. H01J 49/107; G01N 30/8631; G01N 30/8651; G01N 30/7266
USPC ........................................ 250/281, 282, 290
See application file for complete search history.

(56) References Cited

FOREIGN PATENT DOCUMENTS

| | | | |
|---|---|---|---|
| JP | 2008053020 A * | 3/2008 | .......... H01J 49/0031 |
| JP | 2009-192388 A | 8/2009 | |
| JP | 2009192388 A * | 8/2009 | .......... H01J 49/0031 |
| WO | 2004/026448 A1 | 4/2004 | |

OTHER PUBLICATIONS

International Search Report of PCT/JP2014/053015 dated Apr. 15, 2014 [PCT/ISA/210].
Written Opinion for PCT/JP2014/053015 dated Apr. 15, 2014. [PCT/ISA/237].

\* cited by examiner

|  | Analysis Mode | Mass Range | Scan Rate | ESI Volage | APCI Volage |
|---|---|---|---|---|---|
| Event 1 | Q1scan | 10~1000 | 10000u/s | 4kV | 0.1kV |
| Event 2 | Q1scan | 10~1000 | 10000u/s | 4kV | 2kV |
| Event 3 | Q1scan | 10~1000 | 10000u/s | 4kV | 4kV |

Fig. 6A
EVENT 1

Fig. 6B
EVENT 2

Fig. 6C
EVENT 3

Fig. 6D

Fig. 8A
CONVENTIONAL

Fig. 8B
PRESENT EMBODIMENT

Fig. 9

|          | Analysis Mode | Measurement Condition | ESI Voltage | APCI Voltage |
|----------|---------------|-----------------------|-------------|--------------|
| Event 11 | MRM           | Pause 3ms, Dwell 57ms | 4kV         | 0.1kV        |
| Event 12 | MRM           | Pause 3ms, Dwell 57ms | 4kV         | 1kV          |
| Event 13 | MRM           | Pause 3ms, Dwell 57ms | 4kV         | 2kV          |
| Event 14 | MRM           | Pause 3ms, Dwell 57ms | 4kV         | 3kV          |
| Event 15 | MRM           | Pause 3ms, Dwell 57ms | 4kV         | 4kV          |

Fig. 12A
WHEN INTENSITY IS HIGHEST

Fig. 12B
WHEN S/N RATIO IS HIGHEST

MASS SPECTROMETER AND MASS SPECTROMETRY METHOD

CROSS REFERENCE TO RELATED APPLICATIONS

This application is a National Stage of International Application No. PCT/JP2014/053015, filed Feb. 10, 2014, the contents of which are incorporated herein by reference in its entirety.

TECHNICAL FIELD

The present invention relates to a mass spectrometer and mass spectrometry method in which an electrospray ionization (ESI) source and atmospheric pressure chemical ionization (APCI) source are used in combination to ionize the components in a liquid sample and to perform a mass spectrometry.

BACKGROUND ART

For a qualitative or quantitative determination of various components contained in a sample, a liquid chromatograph mass spectrometer (LC/MS) is widely used, which is an apparatus including a liquid chromatograph (LC) unit for temporally separating those components and a mass spectrometer (MS) unit for ionizing the separated components and for performing a mass spectrometry of the ions. In many cases, an electrospray ionization (ESI) source or atmospheric pressure chemical ionization (APCI) source is used as the ionization source in the mass spectrometer unit. The ESI source is used in the case where the component to be analyzed is a high-polarity compound, while the APCI source is used for a low-polarity compound.

A sample which contains a plurality of components often contains a mixture of high-polarity and low-polarity components. As a device for performing a mass spectrometry for such a sample, a mass spectrometer equipped with an ionization source called the "dual ionization source" has been proposed, which includes both the ESI source and the APCI source (for example, see Patent Literature 1). A dual ionization source includes: an ESI probe into which a liquid sample is introduced; an ESI power source which supplies the ESI probe with high voltage (ESI voltage); a needle (corona needle), located near the exit port of the ESI probe, for inducing a corona discharge by supplying high voltage; and an APCI power source which supplies the needle with high voltage (APCI voltage).

The liquid sample and mobile phase which have been separated into components in the liquid chromatograph and introduced into the ESI probe are discharged from this probe in the form of droplets which are electrically charged due to the ESI voltage applied to the ESI probe. In this process, high-polarity components are ionized among the components contained in the sample, while low-polarity components contained in the sample are not ionized at this stage; they are ionized by exchanging electric charges with the mobile phase which is ionized by the corona discharge at the corona needle.

CITATION LIST

Patent Literature

Patent at 1: JP 2005-539358 A

SUMMARY OF INVENTION

Technical Problem

The components contained in a sample have various degrees of polarity, and the optimum values of the ESI and APCI voltages for ionizing those components also vary from one component to another. Therefore, when the dual ionization source is used, the ESI and APCI voltages are set at their average values. However, when the average ESI and APCI voltages are applied, the ionization efficiency for some components may become too low to produce a quantity of ions that can be detected with a sufficient level of intensity for the quantitative determination of those components.

The problem to be solved by the present invention is to provide a mass spectrometer and mass spectrometry method with which a quantity of ions that can be detected with a sufficient level of intensity can be produced for each component contained in the sample, regardless of the degree of polarity or other properties of the component, so as to obtain the mass spectrometry result with a high level of sensitivity and accuracy.

Solution to Problem

The mass spectrometer according to the present invention developed for solving the previously described problem includes:

a) an ionization source including: an ESI probe into which a liquid sample containing one or a plurality of components is introduced; a corona needle located near the exit port of the ESI probe; an ESI voltage supplier for supplying the ESI probe with an ESI voltage; and an APCI voltage supplier for supplying the corona needle with an APCI voltage;

b) an ionization condition storage section for storing a plurality of ionization conditions related to the liquid sample, set by an analysis operator, with the ionization conditions differing from each other in the value of the ESI voltage or/and the value of the APCI voltage;

c) a mass spectrometry executer for conducting a mass spectrometry for an ion generated from the liquid sample using each of the plurality of ionization conditions; and d) a mass spectrometry result selector for selecting, for each of the one or plurality of components, a mass spectrometry result in which the ion is detected with a suitable level of intensity for an analysis, from the mass spectrometry results respectively obtained for the plurality of ionization conditions.

The "mass spectrometry result in which the ion is detected with a suitable level of intensity for an analysis" is normally a mass spectrometry result in which the detection intensity of the ion is at the highest level, but is not limited to this one. For example, the mass spectrometry result selector may be configured to select a mass spectrometry result in which the ratio of the detection intensity of the ion to the noise level (signal-to-noise ratio; S/N ratio) is at the highest level, or to select a mass spectrometry result which shows the highest level of ion detection intensity after the exclusion of the mass spectrometry results in which the ion detection intensity exceeds the upper limit of the dynamic range of the detector.

In the mass spectrometer according to the present invention, a liquid sample is ionized under a plurality of ionization conditions which differ from each other in the value of the ESI voltage or/and APCI voltage, and a mass spectrometry result in which the ion is detected with a suitable level of intensity for an analysis is selected from the mass spectrometry results obtained under those ionization conditions. Therefore, even when a plurality of components having different degrees of polarity are contained in the sample, a quantity of ions that can be detected with a sufficient level of intensity can be produced for each component, so that a highly accurate mass spectrometry result can be obtained.

The mass spectrometer according to the present invention can be suitably used in an LC/MS. In an LC/MS, each of the components separated in the LC column is eluted within a limited period of time. Furthermore, the rate of elution changes within that period of time. In such a case, the mass spectrometry executer should preferably perform the mass spectrometry using the plurality of ionization conditions cyclically.

The mass spectrometer according to the present invention can be used to perform a preliminary measurement for determining the ionization condition to be used in a mass spectrometry for the qualitative or quantitative determination of a component contained in a liquid sample. The qualitative or quantitative determination of the component contained in the liquid sample is achieved, for example, by a selective ion monitoring (SIM) method or multiple reaction monitoring (MRM) method.

Accordingly, the mass spectrometer according to the present invention may further include:

e) an ionization condition determiner for determining, for each of the one or plurality of components, the ionization condition corresponding to the selected mass spectrometry result as an optimum ionization condition.

The mass spectrometry method according to the present invention developed for solving the previously described problem is a method for performing a mass spectrometry for an ion generated from a liquid sample containing one or a plurality of components in an ionization source provided in a mass spectrometer, the ionization source including an ESI source for ionizing the liquid sample by applying an ESI voltage to an ESI probe into which the liquid sample is introduced and an APCI source for ionizing the liquid sample discharged from the ESI probe by applying an APCI voltage to a corona needle located near the exit port of the ESI probe, the method including the steps of:

a) allowing an analysis operator to set a plurality of ionization conditions for the ionization of the liquid sample, with the ionization conditions differing from each other in the value of the ESI voltage or/and the value of the APCI voltage;

b) performing a mass spectrometry for an ion generated from the sample under each of the plurality of ionization conditions; and c) selecting, for each of the one or plurality of components, a mass spectrometry result in which the ion is detected with a suitable level of intensity for an analysis, from the mass spectrometry results respectively obtained for the plurality of ionization conditions.

ADVANTAGEOUS EFFECTS OF THE INVENTION

By using the mass spectrometer or mass spectrometry method according to the present invention, a quantity of ions that can be detected with a sufficient level of intensity will be produced for each component contained in a sample, regardless of the degree of polarity or other properties of the component, so that a mass spectrometry result with a high level of sensitivity and accuracy can be obtained.

DESCRIPTION OF EMBODIMENTS

Figure 1:
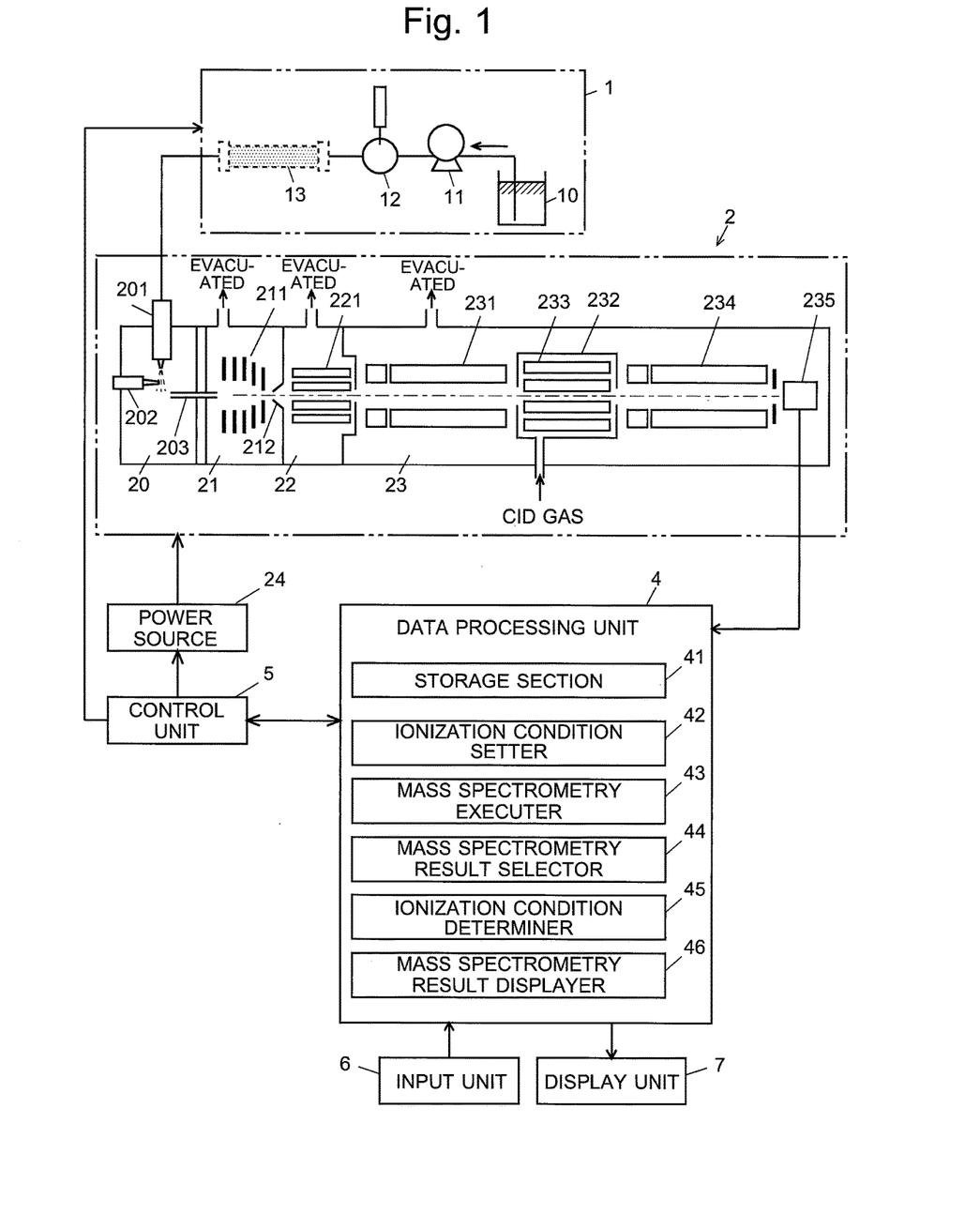
FIG. 1 is a configuration diagram showing the main components in one embodiment of the mass spectrometer according to the present invention.

As one embodiment of the mass spectrometer according to the present invention, a mass spectrometer having a tandem quadrupole configuration is hereinafter described with reference to the drawings. As shown in FIG. 1, the mass spectrometer in the present embodiment is combined with a liquid chromatograph unit 1 to construct a system which operates as a liquid chromatograph mass spectrometer.

In the liquid chromatograph mass spectrometer of the present embodiment, the liquid chromatograph unit 1 includes a mobile phase container 10 holding a mobile phase, a pump 11 for drawing and supplying the mobile phase at a fixed flow rate, an injector 12 for injecting a predetermined amount of prepared sample into the mobile phase, and a column 13 for temporally separating the various compounds contained in the sample. The pump 11 draws the mobile phase from the mobile phase container 10 and supplies it at a fixed flow rate. The liquid sample is injected in a specific amount from the injector 12 and then carried by the stream of the mobile phase into the column 13. The components in the liquid sample are temporally separated within the column 13 and introduced into the mass spectrometer unit 2 with the mobile phase. In the case of a flow injection analysis of a liquid sample, the column 13 is not used; the liquid sample injected from the injector 12 is directly introduced into the mass spectrometer unit 2.

The mass spectrometer unit 2 has the configuration of a multistage differential pumping system including an ionization chamber 20 maintained at substantially atmospheric pressure and an analysis chamber 23 evacuated to a high degree of vacuum by a vacuum pump (not shown), between which first and second intermediate vacuum chambers 21 and are provided having their degrees of vacuum increased in a stepwise manner.

The ionization source in the mass spectrometer of the present embodiment is a dual ionization source including a probe (ESI probe) 201 for the electrospray ionization (ESI) of a liquid sample and a needle (corona needle) for the atmospheric pressure chemical ionization (APCI) of a liquid sample, both of which are provided within the ionization chamber 20. High-polarity components in the liquid sample are primarily ionized by the ESI, while low-polarity components are primarily ionized by the APCI.

The ionization chamber 20 and the first intermediate chamber 21 in the next stage communicate with each other through a thin heated capillary 203. The first intermediate vacuum chamber 21 is separated from the second intermediate vacuum chamber 22 by a skimmer 212 having a small hole at its apex. Ion guides 211 and 221 for transporting ions while focusing them are placed within the first and second intermediate vacuum chambers 21 and 22, respectively. The analysis chamber 23 contains a front quadrupole mass filter (Q1) 231 which separates ions according to their mass-to-charge ratios and a rear quadrupole mass filter (Q3) 234 which also separates ions according to their mass-to-charge ratios, with a collision cell 232 containing a multipole ion guide (q2) 233 placed between the two filters, as well as an ion detector 235.

The power source 24 applies predetermined voltages to the ESI probe 201, corona needle 202, ion guide 211, 221 and 233, the quadrupole mass filters 231 and 234, as well as other elements. In each of the quadrupole mass filters 231 and 234, pre-rod electrodes for correcting the disturbance of the electric field at the inlet end are provided before the main rod electrodes. A voltage which is different from those applied to the main rod electrodes can be applied to the pre-rod electrodes.

In the mass spectrometry unit 2, the liquid sample and the mobile phase which have arrived at the ESI probe 201 to which a high voltage (ESI voltage) is applied from the power source 24 are sprayed from the tip of the ESI probe 201 in the form of droplets having electric charges (charged droplets). The charged droplets are gradually broken into smaller sizes due to the effect of the electrostatic force resulting from the electric charges given to those droplets. In this process, high-polarity components in the liquid sample are ionized, while low-polarity components contained in the sample are not ionized at this stage; they are ionized by exchanging electric charges with the mobile phase after the mobile phase is ionized by the corona discharge at the corona needle 202 induced by the application of a high voltage (APCI voltage).

The ions produced in this manner are sent through the capillary 203 into the first intermediate vacuum chamber 21, where the ions are focused by the ion guide 211, to be sent through the on all hole at the apex of the skimmer 212 into the second intermediate vacuum chamber 22. The ions are once more focused by the ion guide 221 in the second intermediate vacuum chamber 22 and sent into the analysis chamber 23, where the ions are introduced into the space extending along the longitudinal of the front quadrupole mass filter 231.

The mass spectrometer unit 2 of the present embodiment is capable of both MS analysis and MS/MS analysis.

In the case of the MS analysis, a predetermined form of voltage (composed of a radio-frequency voltage and a direct-current voltage superposed on each other) is applied from the power source 24 to each of the front and rear quadrupole mass filters 231 and 234 so that one of the mass filters allows only an ion having a specific mass-to-charge ratio to pass through while the other mass filter allows the passage of the ions over the entire range of mass-to-charge ratios. Ions which have passed through the rear quadrupole mass filter 234 are detected by the ion detector 235. One example of the ion detector 235 is a pulse-counting detector, which generates pulse signals whose number corresponds to the number of incident ions. Those signals are sent to a data processing unit 4 as detection signals.

In the case of the MS/MS analysis, a predetermined form of voltage (composed of a radio-frequency voltage and a direct-current voltage superposed on each other) is applied from the power source 24 to each of the front and rear quadrupole mass filters 231 and 234 so that each of the quadrupole mass filters allows only an ion having a specific mass-to-charge ratio to pass through. Meanwhile, CID gas is continuously or intermittently supplied to the collision cell 232. Among the various ions generated in the ionization chamber 20 and sent into the front quadrupole mass filter 231, only an ion having a specific mass-to-charge ratio corresponding to the voltage applied to the rod electrodes of the front quadrupole mass filter 231 is allowed to pass through this filter 231 and be introduced into the collision cell 232 as the precursor ion. Within the collision cell 232, the precursor ion collides with the CID gas and becomes dissociated, generating various product ions. These product ions are introduced into the rear quadrupole mass filter 234, among which only a product ion having a specific mass-to-charge ratio corresponding to the voltage applied to the rod electrodes of the rear quadrupole mass filter 234 is allowed to pass through this filter 234 and be detected by the ion detector 235.

The data processing unit 4 has a storage section 41 as yell as an ionization condition setter 42, mass spectrometry executer 43, mass spectrometry result selector 44, ionization condition determiner 45, and mass spectrometry result displayer 46 as its functional blocks. Furthermore, the data processing unit 4 is configured to appropriately send and receive signals to and from a control unit 5, which controls the operations of the pump 11 and the injector 12 in the liquid chromatograph unit 1, the power source 24 and the CID gas supplier (not shown) in the mass spectrometer unit 2, as well as other sections of the system. The data processing unit 4 is actually a personal computer, which functions as the data processing unit 4 when a dedicated data processing software program previously installed on the same computer is executed. Additionally, an input unit 6 and display unit 7 are connected to the data processing unit 4.

Embodiments 1-3 of the mass spectrometry method using the liquid chromatograph mass spectrometer of the present embodiment are hereinafter described.

Embodiment 1

The present embodiment is an example of the mass spectrometry method in which a liquid sample which contains components A, B and C is introduced by a flow injection method without using the column 13 in the liquid chromatograph unit 1 and is subjected to an MS scan analysis in the mass spectrometer unit 2. The components A, B and C in the present embodiment are high-polarity, low-polarity and medium-polarity components, respectively. This mass spectrometry method is hereinafter described with reference to the flowchart of FIG. 2.

Figure 2:
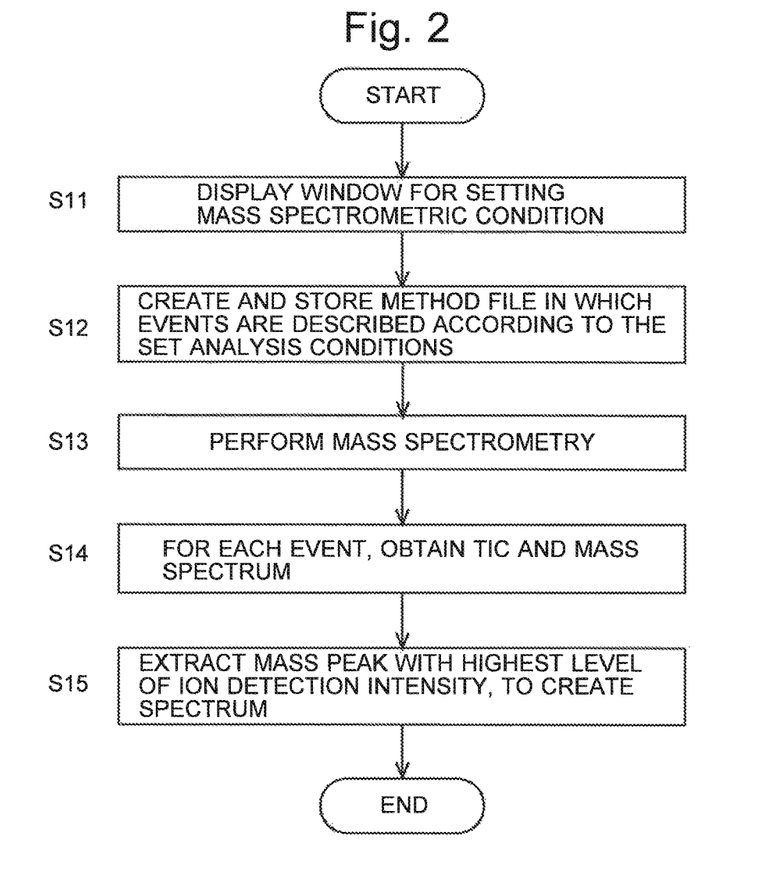
FIG. 2 is a flowchart explaining the mass spectrometry method in Embodiment 1.

Initially, the ionization condition setter 42 displays a window for setting the mass spectrometric condition for the liquid sample on the display unit 7 (Step S11), and prompts an analysis operator to perform the setting. The items of the mass spectrometric condition to be set by the analysis operator include: the mode of the mass spectrometry (Q1scan, Q3 scan, MRM, etc.), range of mass-to-charge ratios, scan rate (in the case of a scan measurement), and ionization conditions for the liquid sample (values of the ESI and APCI voltages). The analysis operator is prompted to set a plurality of ionization conditions with different values of the ESI voltage and/or APCI voltage.

Figure 3:
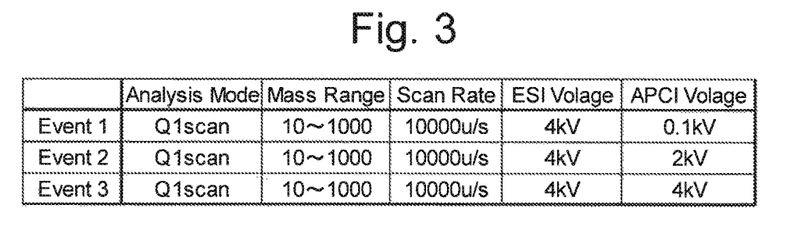
FIG. 3 is a table explaining the analysis conditions used in the mass spectrometry method in Embodiment 1.

After the mass spectrometric conditions are set by the analysis operator, the ionization condition setter 42 stores the set mass spectrometric conditions in the storage section 41 (Step S12). In the present embodiment, as shown in FIG. 3, three mass spectrometric conditions are set for three events 1-3 with different APCI voltages. Events 1-3 differ from each other in the magnitude of the APCI voltage applied to ionize the liquid sample. Specifically, the relative relationship between the ESI voltage and the APCI voltage is set in each of the ionization conditions in such a manner that high-polarity components, for which the ESI is suitable, will be efficiently generated in Event 1, whereas low-polarity components, for which the APCI is suitable, will be efficiently ionized in Event 3. Event 2 is set as an intermediate ionization condition between Events 1 and 3.

Figure 4:
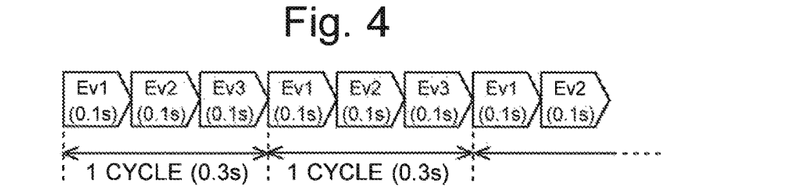
FIG. 4 is a diagram illustrating the flow of the analysis in the mass spectrometry method in Embodiment 1.
Figure 5:
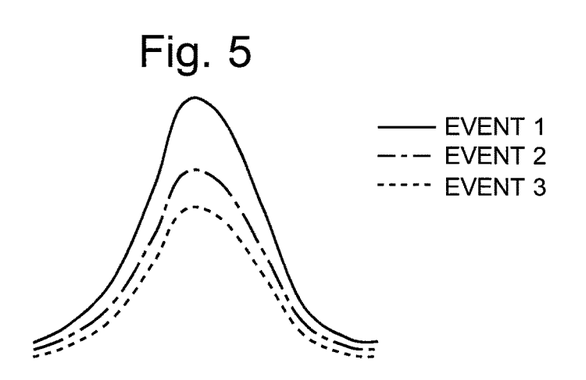
FIG. 5 is a diagram illustrating the total ion chromatograms (TIC) obtained in Embodiment 1.

Subsequently, the mass spectrometry executer 43 performs a mass spectrometry according to the set and stored conditions. Specifically, it cyclically performs a mass spectrometry with Events 1-3 in each cycle (FIG. 4; Step S13), and obtains the total ion chromatogram (TIC) and mass spectrum for each event (Step S14). The mass spectrometry result displayer 46 displays the TICs and mass spectra on the display unit 7.

The TICs and the mass spectra obtained by the measurement are shown in FIG. 5 and FIGS. 6A-6C, respectively. The highest level of the ion detection intensity of the high-polarity component A is recorded in Event 1, that of the low-polarity component B is recorded in Event 3, and that of the medium-polarity component C is recorded in Event 2. The ion detection intensity reflects the amount of generated ions. That is to say, these results demonstrate that the condition of Event 1 is most suitable for the ionization of the high-polarity component A, the condition of Event 3 is most suitable for the ionization of the low-polarity component B, and the condition of Event 2 is most suitable for the medium-polarity component C.

Figure 6A:
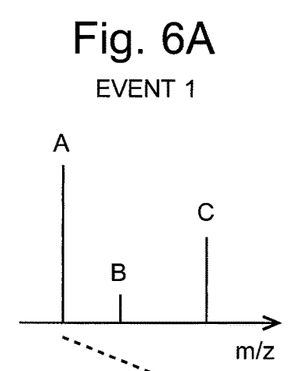
FIGS. 6A-6D are diagrams illustrating the mass spectra created in Embodiment 1.
Figure 6B:
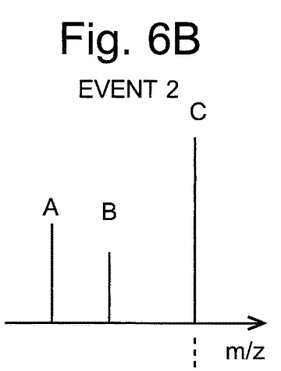
Figure 6C:
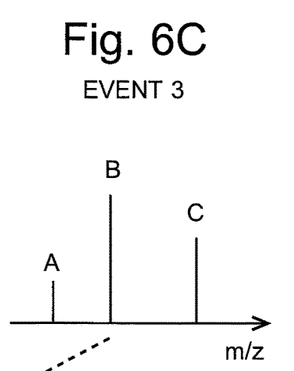
Figure 6D:
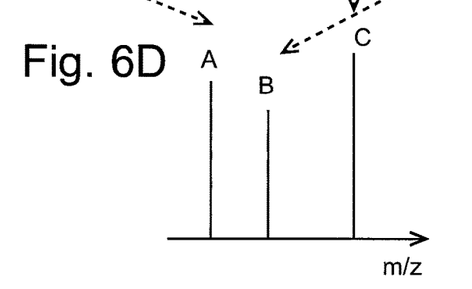

Ultimately, for each component, the mass spectrometry result selector 44 compares the intensities of the ions detected in Events 1-3 and extracts one peak having the highest detection intensity to reconstruct the mass spectrum (FIG. 6D). The mass spectrometry result displayer 46 displays the reconstructed mass spectrum on the display unit 7. In this manner, for each of the components having different degrees of polarity contained in the sample, a quantity of ions that can be detected with a sufficient level of intensity can be produced, so that a mass spectrometry result with a high level of sensitivity and accuracy can be obtained.

Embodiment 2

In the mass spectrometry method of Embodiment 2, the condition for the multiple reaction monitoring (MRM) analysis of an unknown liquid sample ("MRM method") is optimized. Specifically, the description in the present embodiment deals with the method of optimizing the analysis condition (MRM method) for performing an MRM analysis of an unknown liquid sample with a high-polarity component A, low-polarity component B and medium-polarity component C as the target components.

In the MRM analysis, for each target component, an ion having a specific mass-to-charge ratio is selectively allowed to pass through the front quadrupole mass filter 231 as the precursor ion, and then, this precursor ion is made to collide with the CID gas in the collision cell 232, whereby the ion is fragmented into various product ions. Subsequently, in the rear quadrupole mass filter 234, a product ion having a specific mass-to-charge ratio is selectively allowed to pass through and be detected by the ion detector 235. Accordingly, in order to perform the MRM analysis, it is necessary to previously determine, for each component, the mass-to-charge ratio of the precursor ion to be selected with the front quadrupole mass filter 231 as well as the mass-to-charge ratio of the product ion to be selected with the rear quadrupole mass filter 234. In the following description, the combination of the precursor ion and product ion in the MRM measurement is called the "MRM transition".

MRM analyses are mainly performed for the qualitative or quantitative determination of a target component. The higher the detection intensity of the product ion is, the more accurate the analysis becomes. Therefore, normally, in addition to the MRM transition, the collision energy (CE) which is imparted in the process of making the precursor ion collide with the CID gas in the collision cell 232 is also optimized so as to maximize the generation efficiency of the product ions. Furthermore, in the present embodiment, the ionization condition is also optimized so as to maximize the generation efficiency of the precursor ion within the ionization chamber 20.

Figure 7:
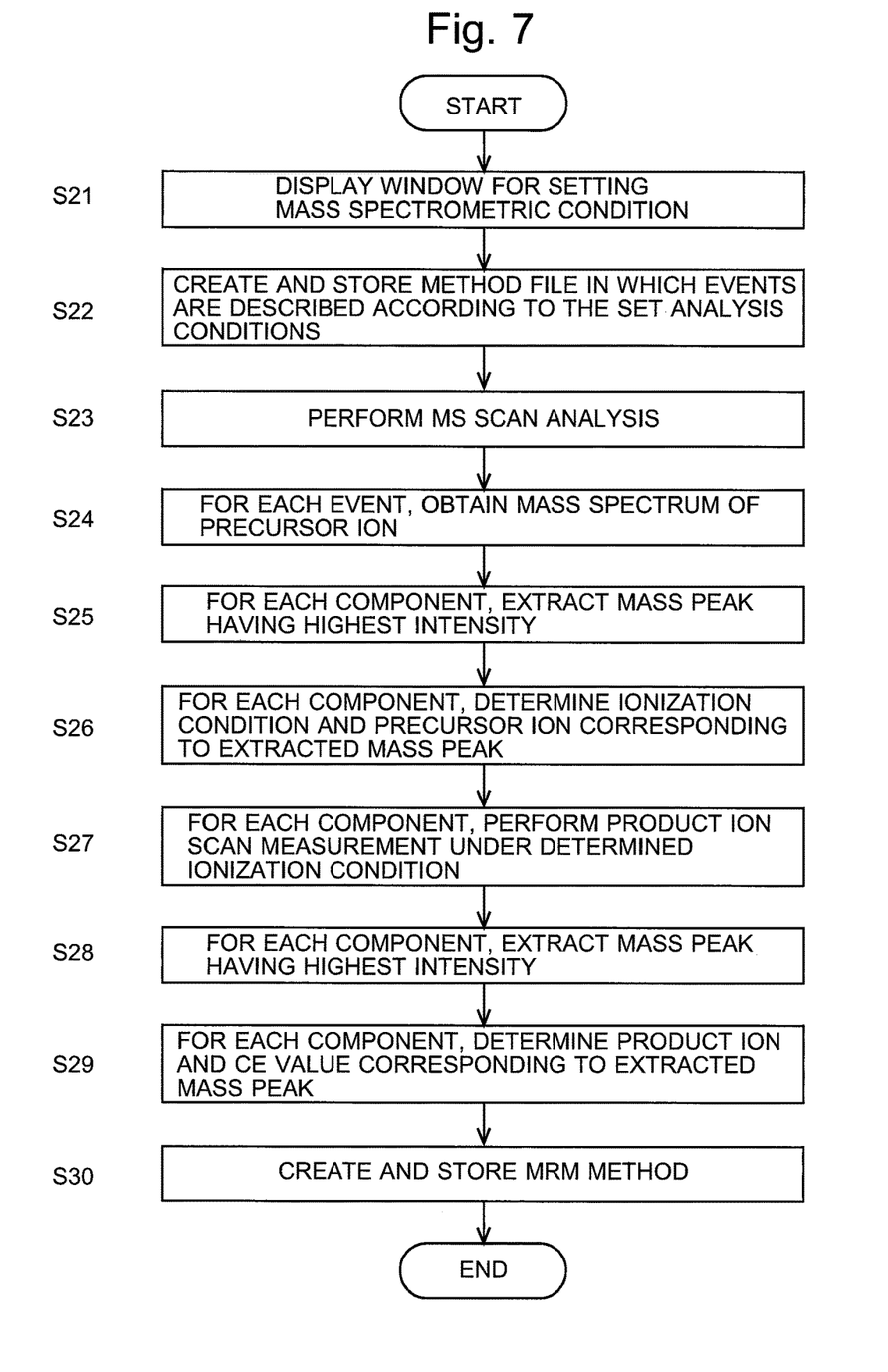
FIG. 7 is a flowchart explaining the mass spectrometry method in Embodiment 2.

The procedure for optimizing the MRM method is hereinafter described with reference to the flowchart of FIG. 7.

Initially, the ionization condition setter 42 displays a window for setting the mass spectrometric condition for the liquid sample and the mass spectrometric condition for determining the precursor ion on the display unit 7 (Step S21), and prompts an analysis operator to perform the setting. The items of the mass spectrometric conditions to be set by the analysis operator are the same as mentioned in Embodiment 1. The ionization condition setter 42 stores the set mass spectrometric conditions as the conditions for the analyses ("events") in the storage section 41 (Step S22). In the present embodiment. Events 1-3 as shown in FIG. 3 are used.

Next, the mass spectrometry executer 43 performs a mass spectrometry (Q1scan) according to the set conditions (Step S23) and obtains a mass spectrum of the precursor ion for each event (Step S24). The mass spectrometry result displayer 46 displays these mass spectra on the display unit 7. The mass spectrometry result selector 44 compares the mass spectra obtained for each event and extracts the mass peak having the highest intensity for each component (Step S25). The ionization condition determiner 45 determines, for each component, the ionization condition used in the event in which the extracted mass peak has appeared, and also sets the ion corresponding to that mass peak as the precursor ion (Step S26). At this stage, the ionization conditions in Events 1, 3 and 2 are determined as the ionization conditions for the high-polarity component A, low-polarity component B and medium-polarity component C, respectively. It is also possible to extract a plurality of mass peaks in descending order of intensity and set a plurality of precursor ions, instead of extracting a single mass peak having the highest intensity in the previously described manner. For example, a plurality of precursor ions need to be set in an MRM analysis which uses one MRM transition for quantitative determination and another MRM transition for the checking.

The subsequent steps are similar to those conventionally used for the optimization of the MRM method, and therefore, will be only briefly described.

After the ionization condition and the precursor ion for each target compound are determined, the mass spectrometry executer 43 once more performs the product ion scan measurement, using the set ionization conditions, with each condition including a different CE value (Step S27). More specifically, in the front quadrupole mass filter 231, the previously set precursor ion is selectively allowed to pass through. In the collision cell 232, the precursor ion is fragmented into product ions. In the rear quadrupole mass filter 234, the mass-to-charge ratio at which the ions are allowed to pass through is continuously changed to obtain a product ion scan spectrum. The mass spectrometry result displayer 46 displays, on the display unit 7, the product ion scan spectra respectively obtained under the plurality of conditions with different CE values. The mass spectrometry result selector 44 compares the obtained product ion scan spectra for each component to extract the mass peak having the highest intensity (Step S28), and determines the product ion and the CE value corresponding to that mass peak (Step S29). An MRM method which includes the ionization condition, MRM transition (the mass-to-charge ratio of the precursor ion and that of the product ion) and CE value determined in this manner is created and stored in the storage section 41 (Step S30). It should be noted that, if the product ion scan measurement is performed at a high scan rate, a mass discrepancy may arise between the mass-to-charge ratio in the product ion scan measurement and the mass-to-charge ratio in the MRM analysis. In such a case, it is preferable to create the MRM method after performing the mass correction based on the calibration table previously created for the mass spectrometer.

Figure 8A:
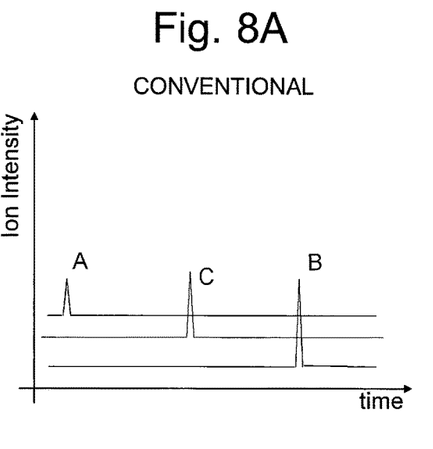
FIGS. 8A and 8B are diagrams illustrating the mass chromatogram obtained by an MRM measurement using the mass spectrometry method in Embodiment 2.
Figure 8B:
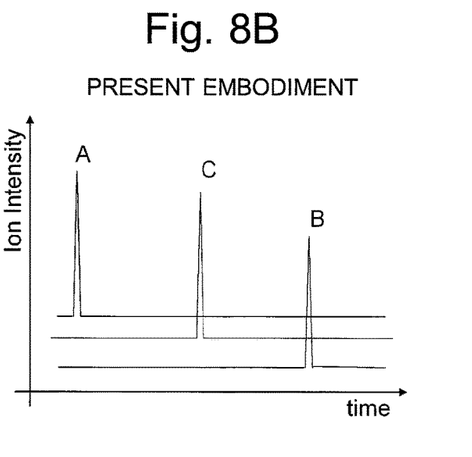

In the conventional case of creating the MRM method, the ionization condition in the ionization chamber 20 is not optimized. Therefore, depending on the degree of polarity of the component, the generation efficiency of the ion may become too low to obtain a sufficient level of detection intensity in the MRM measurement (FIG. 8A). By optimizing the ionization condition for each component in the process of optimizing the MRM method, a quantity of ions that can be detected with a sufficient level of intensity can be produced, regardless of the deuce of polarity of the component, so that the MRM measurement can be performed with a high level of sensitivity (FIG. 8B).

Embodiment 3

In Embodiment 3, an example of the method of obtaining an optimum mass chromatogram in an MRM analysis using an LC/MS is described. The target component in the present embodiment is the medium-polarity component C. The MRM transition and the CE value component C are previously determined with reference to a compound database or similar information.

Figure 9:
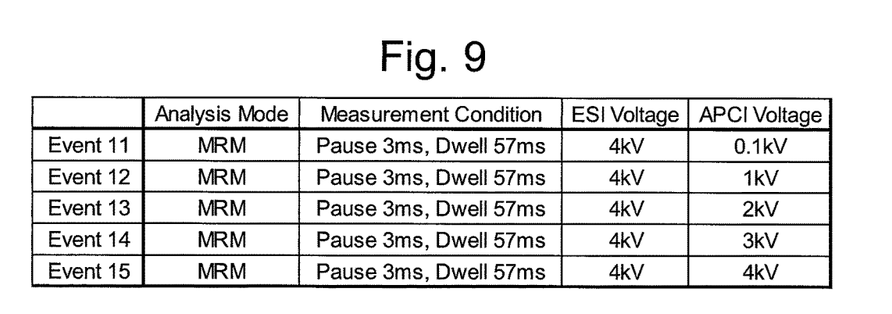
FIG. 9 is a table explaining the analysis conditions used in the mass spectrometry method in Embodiment 3.
Figure 10:
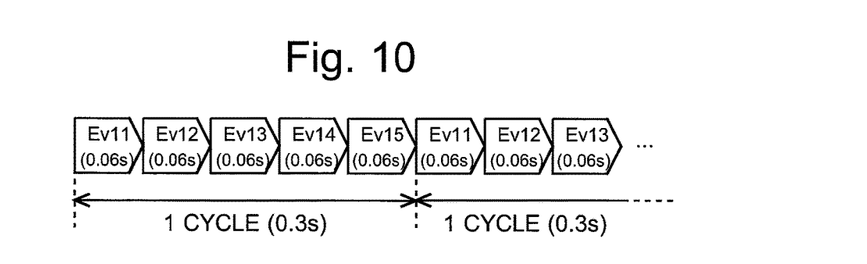
FIG. 10 is a diagram illustrating the flow of the analysis in the mass spectrometry method in Embodiment 3.

In the present embodiment, an analysis operator sets a plurality of MRM analysis conditions with different APCI voltages (Events 11-15; FIG. 9) in the mass spectrometry setting window displayed on the display 7 by the ionization condition setter 42. The mass spectrometry executer 43 repeatedly performs Events 11-15 and obtains a mass chromatogram for each event (FIG. 10). Subsequently, the mass spectrometry result selector 44 calculates the signal-to-noise (S/N) ratio value of the mass chromatogram for each event to extract a mass chromatogram having the highest S/N ratio value. For example, the S/N ratio value of the mass chromatograms can be determined by calculating the ratio of the peak intensity in the chromatogram to the RMS value of the signal level within a region exclusive of the peak.

Figure 11:
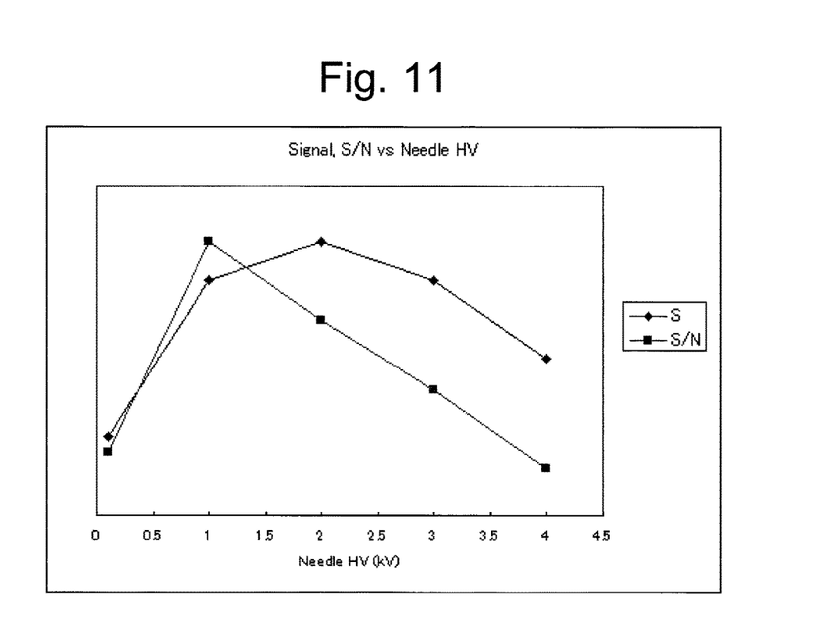
FIG. 11 is a graph explaining the relationship between the signal-to-noise (S/N) ratio value and the ionization condition in the mass spectrometry method in Embodiment 3.
Figure 12A:
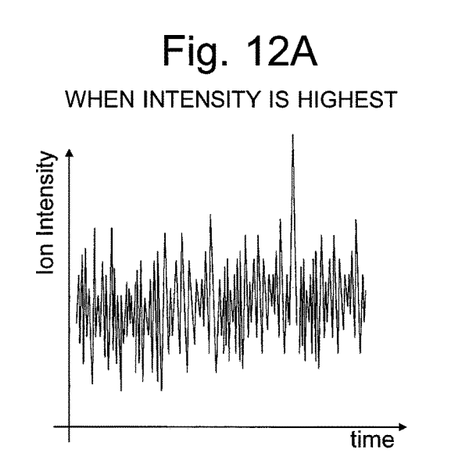
FIGS. 12A and 12B show a comparison of a mass chromatogram obtained under an ionization condition which maximizes the ion detection intensity and a mass chromatogram obtained under an ionization condition which maximizes the S/N ratio value in the mass spectrometry method in Embodiment 3.
Figure 12B:
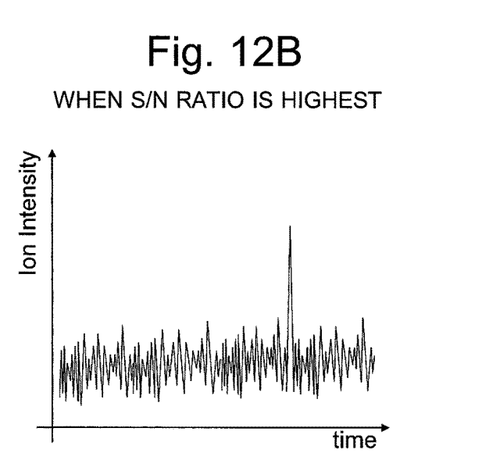

As shown in FIG. 11, the ionization condition which maximizes the S/N ratio value (APCI voltage: 1 kV) may differ from the ionization condition which maximizes the peak intensity (APCI voltage: 2 kV). In such a case, selecting the condition which maximizes the peak intensity may result in an insufficient difference between the peak and noise levels, making the peak difficult to identify despite the increased peak intensity (FIG. 12A). In such a case, selecting the ionization condition which maximizes the S/N ratio value is more preferable, as in the present embodiment.

Any of the previously described embodiments is a mere example and can be appropriately modified according to the spirit of the present invention. In the previous embodiments, the same ESI voltage is set and only the APCI voltage is varied among the plurality of ionization conditions. It is also possible to set a plurality of ionization conditions which differ from each other in both the ESI voltage and the APCI voltage, or a plurality of ionization conditions which only differ from each other in the ESI voltage.

In the previous embodiments, a mass spectrometer having a tandem quadrupole configuration was used as one example. However, the present invention is not limited to the quadrupole type; e.g. a time-of-flight mass spectrometer may also be used. Furthermore, the present invention is not only applicable in the examples of the MS or MS/MS measurement as described in the previous embodiments, but is also applicable in other measurement methods (e.g. SIM measurement) or in an MS$^n$ analysis in a mass spectrometer including an ion trap.

REFERENCE SIGNS LIST

1 . . . Liquid Chromatograph Unit
   10 . . . Mobile Phase Container
   11 . . . Pump
   12 . . . Injector
   13 . . . Column
2 . . . Mass Spectrometer Unit
   20 . . . Ionization Chamber
      201 . . . ESI Probe
      202 . . . Corona Needle
      203 . . . Heated Capillary
   21 . . . First Intermediate Vacuum Chamber
      211 . . . Ion Guide
      212 . . . Skimmer
   22 . . . Second Intermediate Vacuum Chamber
      221 . . . Ion Guide
   23 . . . Analysis Chamber
      231 . . . Front Quadrupole Mass Filter
      232 . . . Collision Cell
      233 . . . Ion Guide
      234 . . . Rear Quadrupole Mass Filter
      235 . . . Ion Detector
   24 . . . Power Source
4 . . . Data Processing Unit
   41 . . . Storage Section
   42 . . . Ionization Condition Setter
   43 . . . Mass Spectrometry Executer
   44 . . . Mass Spectrometry Result Selector
   45 . . . Ionization Condition Determiner
   46 . . . Mass Spectrometry Result Displayer
5 . . . Control Unit
6 . . . Input Unit
7 . . . Display Unit

The invention claimed is:

1. A liquid chromatograph mass spectrometer, comprising:
   a) an ionization source including: an ESI probe into which a liquid sample containing one or a plurality of components separated from each other in a column of a liquid chromatograph is introduced; a corona needle located near an exit port of the ESI probe; an ESI voltage supplier for supplying the ESI probe with an ESI voltage; and an APCI voltage supplier for supplying the corona needle with an APCI voltage;
   b) an ionization condition storage section for storing a plurality of ionization conditions related to the liquid sample, set by an analysis operator, with the ionization conditions differing from each other in a value of the ESI voltage or/and a value of the APCI voltage;
   c) a mass spectrometry executer for conducting a mass spectrometry for an ion generated from the one or the plurality of components using the plurality of ionization conditions cyclically and obtaining a plurality of mass chromatograms each of which corresponds to each of the plurality of ionization conditions; and
   d) a mass spectrometry result selector for selecting, for each of the one or the plurality of components, a mass spectrometry result in which the ion is detected with a suitable level of intensity for an analysis, from the mass spectrometry results respectively obtained for the plurality of ionization conditions based on the plurality of mass chromatograms.

2. The liquid chromatograph mass spectrometer according to claim 1, wherein the mass spectrometry result selector selects a mass spectrometry result in which a detection intensity of the ion is at a highest level.

3. The liquid chromatograph mass spectrometer according to claim 1, wherein the mass spectrometry result selector selects a mass spectrometry result in which a ratio of a detection intensity of the ion to a noise level is at a highest level.

4. The liquid chromatograph mass spectrometer according to claim 1, comprising:
   e) an ionization condition determiner for determining, for each of the one or plurality of components, the ionization condition corresponding to the selected mass spectrometry result as an optimum ionization condition.

5. The liquid chromatograph mass spectrometer according to claim 1, comprising:
   f) a display unit; and
   g) a mass spectrometry result displayer for displaying, on the display unit, the mass spectrometry result selected by the mass spectrometry result selector.

6. A method for performing a liquid chromatograph mass spectrometry for an ion generated from a liquid sample containing one or a plurality of components separated from each other in a column of a liquid chromatograph in an ionization source provided in a mass spectrometer, the ionization source including an ESI source for ionizing the liquid sample by applying an ESI voltage to an ESI probe into which the liquid sample is introduced and an APCI source for ionizing the liquid sample discharged from the ESI probe by applying an APCI voltage to a corona needle located near an exit port of the ESI probe, the method comprising steps of:
   a) allowing an analysis operator to set a plurality of ionization conditions for an ionization of the liquid sample, with the ionization conditions differing from each other in a value of the ESI voltage or/and a value of the APCI voltage;
   b) performing a mass spectrometry for an ion generated from the one or the plurality of components using the plurality of ionization condition cyclically and obtaining a plurality of mass chromatograms each of which corresponds to each of the plurality of ionization conditions; and
   c) selecting, for each of the one or the plurality of components, a mass spectrometry result in which the ion is detected with a suitable level of intensity for an analysis, from the mass spectrometry results respectively obtained for the plurality of ionization conditions based on the plurality of mass chromatograms.

7. The liquid chromatograph mass spectrometer according to claim 2, comprising:
   e) an ionization condition determiner for determining, for each of the one or plurality of components, the ionization condition corresponding to the selected mass spectrometry result as an optimum ionization condition.

8. The liquid chromatograph mass spectrometer according to claim 3, comprising:
   e) an ionization condition determiner for determining, for each of the one or plurality of components, the ionization condition corresponding to the selected mass spectrometry result as an optimum ionization condition.

9. The liquid chromatograph mass spectrometer according to claim 2, comprising:
   f) a display unit; and
   g) a mass spectrometry result displayer for displaying, on the display unit, the mass spectrometry result selected by the mass spectrometry result selector.

10. The liquid chromatograph mass spectrometer according to claim 3, comprising:
    f) a display unit; and
    g) a mass spectrometry result displayer for displaying, on the display unit, the mass spectrometry result selected by the mass spectrometry result selector.

11. The liquid chromatograph mass spectrometer according to claim 4, comprising:
    f) a display unit; and
    g) a mass spectrometry result displayer for displaying, on the display unit, the mass spectrometry result selected by the mass spectrometry result selector.

12. The liquid chromatograph mass spectrometer according to claim 7, comprising:
    f) a display unit; and
    g) a mass spectrometry result displayer for displaying, on the display unit, the mass spectrometry result selected by the mass spectrometry result selector.

13. The liquid chromatograph mass spectrometer according to claim 8, comprising:
    f) a display unit; and
    g) a mass spectrometry result displayer for displaying, on the display unit, the mass spectrometry result selected by the mass spectrometry result selector.

* * * * *